US010660612B2

(12) United States Patent
Cho et al.

(10) Patent No.: US 10,660,612 B2
(45) Date of Patent: May 26, 2020

(54) ULTRASOUND PROBE AND ULTRASOUND IMAGING DEVICE

(71) Applicant: SAMSUNG ELECTRONICS CO., LTD., Suwon-si (KR)

(72) Inventors: Kyung Il Cho, Seoul (KR); Jong Keun Song, Yongin-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 601 days.

(21) Appl. No.: 15/325,263

(22) PCT Filed: Jul. 10, 2014

(86) PCT No.: PCT/KR2014/006215
§ 371 (c)(1),
(2) Date: Jan. 10, 2017

(87) PCT Pub. No.: WO2016/006739
PCT Pub. Date: Jan. 14, 2016

(65) Prior Publication Data
US 2017/0156697 A1     Jun. 8, 2017

(51) Int. Cl.
*A61B 8/00*     (2006.01)
*G01N 29/24*     (2006.01)
(Continued)

(52) U.S. Cl.
CPC ............... *A61B 8/4494* (2013.01); *A61B 8/00* (2013.01); *A61B 8/145* (2013.01); *A61B 8/4444* (2013.01);
(Continued)

(58) Field of Classification Search
CPC ......... A61B 8/4494; A61B 8/00; A61B 8/145; A61B 8/4444; A61B 8/5207;
(Continued)

(56) References Cited

U.S. PATENT DOCUMENTS

| 6,318,179 B1 | 11/2001 | Hamilton et al. | |
| 2003/0139664 A1* | 7/2003 | Hunt | A61B 8/00 600/407 |

(Continued)

FOREIGN PATENT DOCUMENTS

| EP | 2533241 A2 | 12/2012 |
| JP | 2006110140 A | 4/2006 |

(Continued)

OTHER PUBLICATIONS

Communication dated Jul. 31, 2018, issued by the Korean Intellectual Property Office in counterpart Korean Patent Application No. 10-2017-7000268.

(Continued)

*Primary Examiner* — Lindsey G Wehrheim

(74) *Attorney, Agent, or Firm* — Sughrue Mion, PLLC

(57) ABSTRACT

An embodiment of the disclosure provides an ultrasound probe including a single large-area ASIC in which a plurality of ultrasonic transducer elements are bonded. According to an embodiment, an ultrasound probe comprises: a transducer array including a plurality of transducer elements configured to transmit or receive ultrasound; and an integrated circuit, in which the transducer array is bonded, including a plurality of driving elements corresponding to the plurality of transducer elements, wherein the integrated circuit comprises a time delay table configured to output time delay information regarding respective ultrasound transmission and reception of the plurality of transducer elements.

16 Claims, 3 Drawing Sheets

(51) Int. Cl.
*G10K 11/34* (2006.01)
*A61B 8/14* (2006.01)
*A61B 8/08* (2006.01)
*B06B 1/02* (2006.01)
*B06B 1/06* (2006.01)

(52) U.S. Cl.
CPC .......... *A61B 8/5207* (2013.01); *B06B 1/0207* (2013.01); *B06B 1/0607* (2013.01); *G01N 29/24* (2013.01); *G01N 29/2406* (2013.01); *G01N 29/2437* (2013.01); *G10K 11/346* (2013.01)

(58) Field of Classification Search
CPC .... B06B 1/0207; B06B 1/0607; G01N 29/24; G01N 29/2406; G01N 29/2437; G01K 11/346
See application file for complete search history.

(56) References Cited

U.S. PATENT DOCUMENTS

| | | | |
|---|---|---|---|
| 2004/0220475 | A1 | 11/2004 | Szabo et al. |
| 2007/0244392 | A1 | 10/2007 | Tezuka |
| 2009/0112091 | A1 | 4/2009 | Chiang et al. |
| 2009/0146695 | A1 | 6/2009 | Schweizer et al. |
| 2014/0133270 | A1 | 5/2014 | Hsia et al. |

FOREIGN PATENT DOCUMENTS

| | | |
|---|---|---|
| JP | 2009194934 A | 8/2009 |
| JP | 2012118060 A | 6/2012 |
| KR | 10-2012-0136453 A | 12/2012 |

OTHER PUBLICATIONS

International Search Report dated Mar. 31, 2015, issued by the International Searching Authority in counterpart International Application No. PCT/KR2014/006215 (PCT/ISA/210).
Communication dated Jan. 18, 2018, issued by the Korean Intellectual Property Office in corresponding Korean Application No. 10-2017-7000268.
Communication dated Jan. 30, 2018, from the European Patent Office in counterpart European Application No. 14897098.1.
Communication dated Jan. 28, 2019, issued by the Korean Intellectual Property Office in corresponding Korean Application No. 10-2017-7000268.
Communication dated Apr. 8, 2019, issued by the Korean Intellectual Property Office in corresponding Korean Application No. 10-2017-7000268.

\* cited by examiner

[Fig. 1]
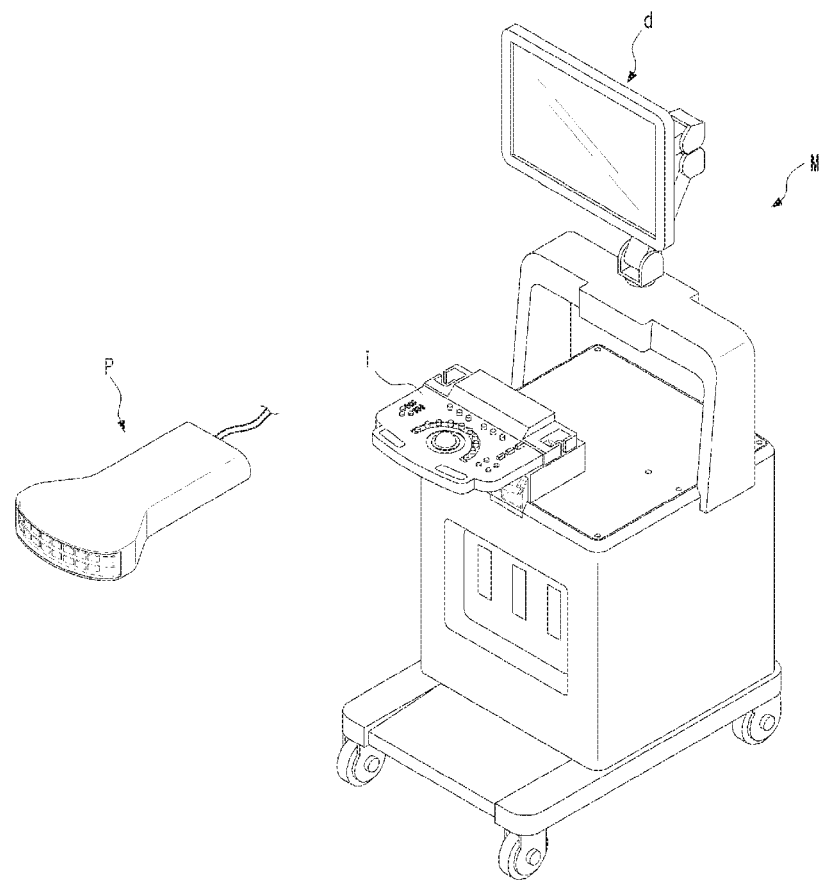
[Fig. 2]
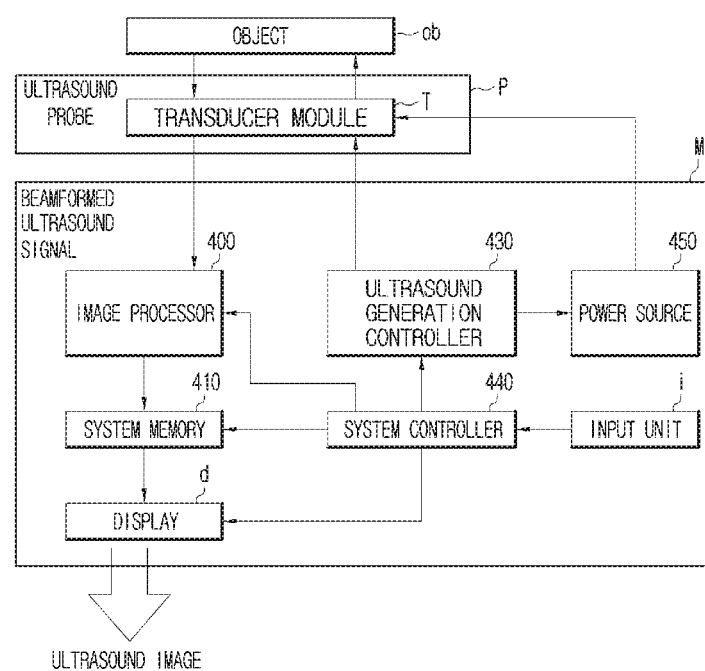

[Fig. 3]
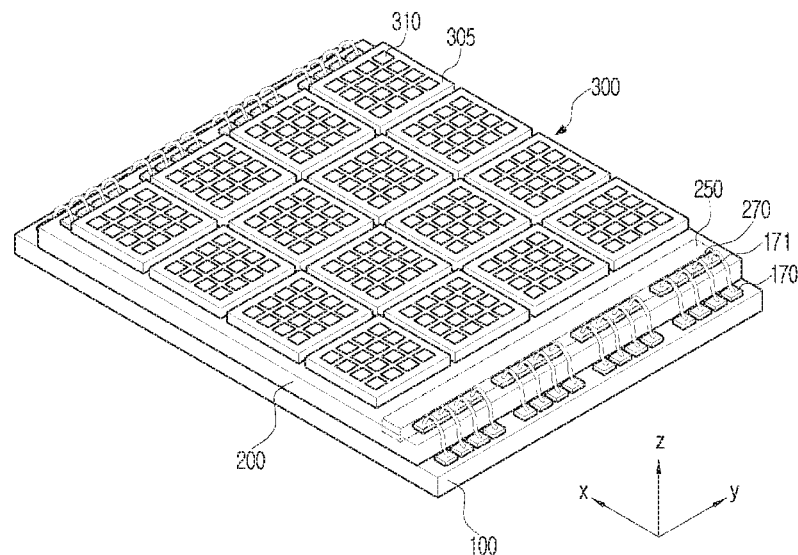
[Fig. 4]
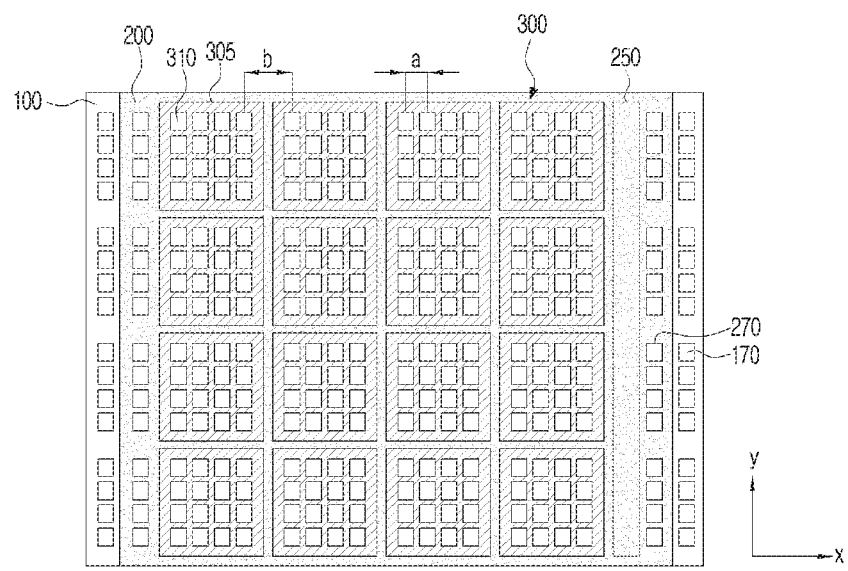
[Fig. 5]
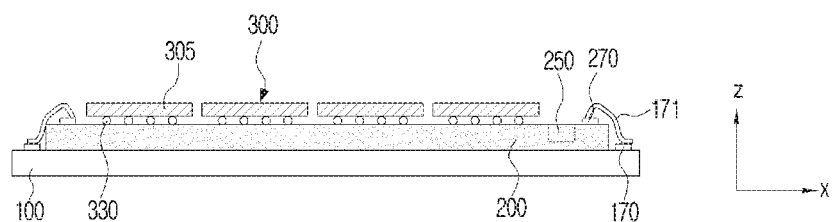

[Fig. 6]
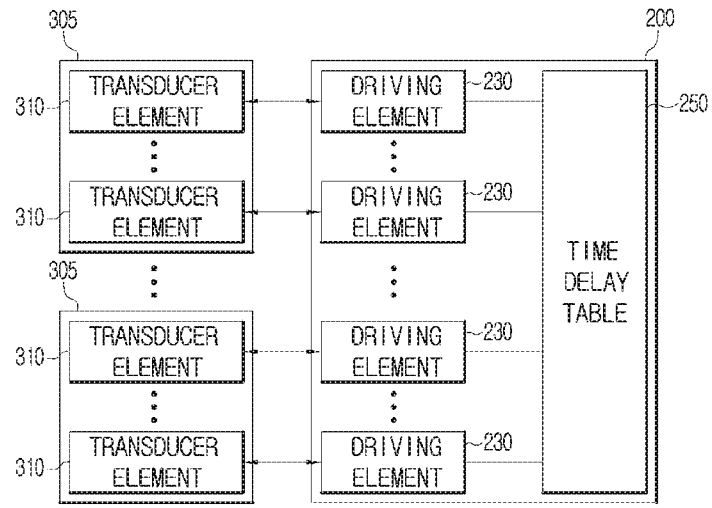
[Fig. 7]
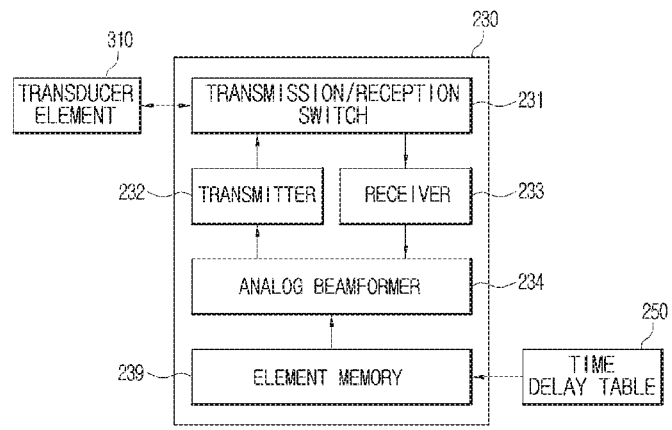
[Fig. 8]
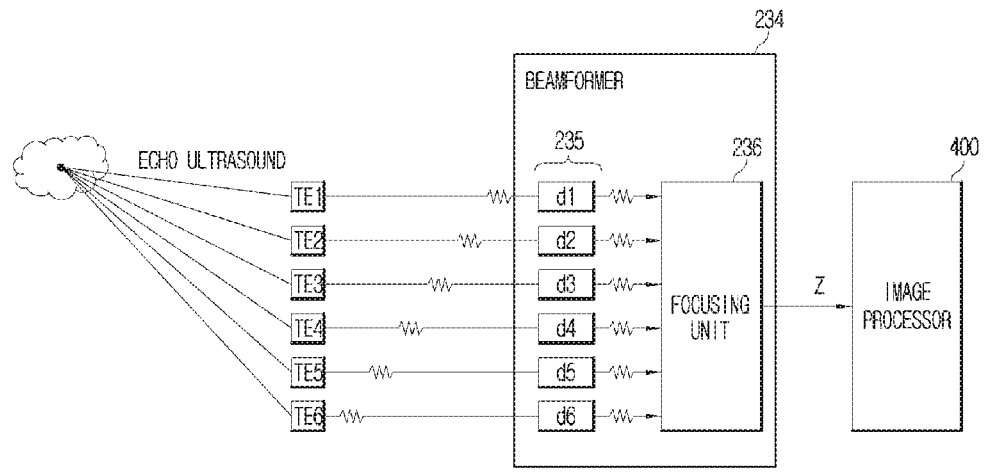

ULTRASOUND PROBE AND ULTRASOUND IMAGING DEVICE

TECHNICAL FIELD

The present disclosure relates to an ultrasound imaging device.

BACKGROUND ART

An ultrasound imaging device is a device for irradiating ultrasound from the surface of an object toward a target portion of the inside of the object, and obtaining images of cross sections of soft tissue or blood flows in an invasive way by receiving reflected echo ultrasound.

The ultrasound imaging device has an advantage of being compact and inexpensive and able to display diagnostic images in real time, as compared with other diagnostic imaging devices, such as X-ray devices, Computerized Tomography (CT) scanners, Magnetic Resonance Imaging (MRI) devices, nuclear medicine diagnostic devices, etc. It has another advantage of high safety because it is free from the risk of radiation exposure. Accordingly, it is being widely used for diagnosis of heart, abdomen, urinary organs as well as obstetric organs.

The ultrasound imaging device includes an ultrasound probe for transmitting ultrasound to an object and receiving echo ultrasound reflected from the object to obtain an image of an internal portion of the object.

DISCLOSURE

Technical Problem

An embodiment of the disclosure provides an ultrasound probe including a single large-area ASIC in which a plurality of ultrasonic transducer elements are bonded.

Technical Solution

According to an embodiment, an ultrasound probe comprises: a transducer array including a plurality of transducer elements configured to transmit or receive ultrasound; and an integrated circuit, in which the transducer array is bonded, including a plurality of driving elements corresponding to the plurality of transducer elements, wherein the integrated circuit comprises a time delay table configured to output time delay information regarding respective ultrasound transmission and reception of the plurality of transducer elements.

According to an embodiment, an ultrasound imaging device comprises: an ultrasound probe including a transducer array including a plurality of transducer elements configured to transmit or receive ultrasound, and an integrated circuit, in which the transducer array is bonded, including a plurality of driving elements corresponding to the plurality of transducer elements and a time delay table configured to output time delay information regarding respective ultrasound transmission and reception of the plurality of transducer elements; and a main body configured to generate an ultrasound image based on a signal output from the ultrasound probe.

Advantageous Effects

According to embodiments of the present disclosure, production yield may be improved by installing a plurality of transducer elements in a single large-area ASIC by SOC bonding.

DESCRIPTION OF DRAWINGS

FIG. 1 is a perspective view of an exemplary ultrasound imaging device;

FIG. 2 is a block diagram of an exemplary ultrasound imaging device;

FIG. 3 is a perspective view of an exemplary transducer module of an ultrasound probe;

FIG. 4 is a plan view of an exemplary transducer module of an ultrasound probe;

FIG. 5 is a side view of an exemplary transducer module of an ultrasound probe;

FIG. 6 shows an architecture of an ASIC for transmitting and receiving ultrasound;

FIG. 7 shows a detailed configuration of a driving element of FIG. 6; and

FIG. 8 conceptually shows a beamforming method of a beamformer included in the driving element.

BEST MODE

Embodiments of the present disclosure will now be described in detail with reference to accompanying drawings.

FIG. 1 is a perspective view of an exemplary ultrasound imaging device, and FIG. 2 is a block diagram of an exemplary ultrasound imaging device. FIG. 3 is a perspective view of an exemplary transducer module of an ultrasound probe, FIG. 4 is a plan view of an exemplary transducer module of an ultrasound probe, and FIG. 5 is a side view of an exemplary transducer module of an ultrasound probe.

As shown in FIGS. 1 and 2, an ultrasound imaging device includes an ultrasound probe p for irradiating ultrasound to an object ob, receiving echo ultrasound from the object ob, and converting the echo ultrasound to an electric signal (hereinafter, referred to as an ultrasound signal), and a main body M for generating an ultrasound image based on the ultrasound signal. As shown in FIG. 1, the main body M may be a workstation connected to the ultrasound probe P and equipped with an input unit i and a display d.

The ultrasound probe p collects information regarding a target portion of the object ob by means of ultrasound.

Referring to FIG. 2, the ultrasound probe p may include a transducer module T for generating and irradiating ultrasound to an internal target portion of the object ob and receiving echo ultrasound.

The transducer module T generates ultrasound based on an applied pulse or alternate current (AC) signal and irradiates the ultrasound to the object ob, and the ultrasound irradiated to the object ob is reflected off from the internal target portion of the object ob. The transducer module T receives the reflected echo ultrasound and generates an ultrasound signal x by converting the received echo ultrasound to an electric signal.

The transducer module T receives power from an external power supply, or an internal condenser, e.g., a battery. Piezoelectric vibrators or thin films constituting the transducer module T vibrate according to the applied power, and thus produce ultrasound. Once receiving the echo ultrasound, the piezoelectric vibrators or thin films forming the transducer module T vibrate according to the received echo ultrasound, generate AC current with a frequency corresponding to the vibration frequency, and convert the ultrasound to an electric signal x (hereinafter, called an ultrasound signal).

More specifically, referring to FIG. 3, the transducer module T includes a transducer array 300 for transmitting and receiving ultrasound, an integrated circuit 200 in which the transducer array 300 is bonded, and a printed circuit board 100 on which the integrated circuit 200 is mounted.

The transducer array 300 includes a plurality of transducer elements 310 for transmitting and receiving ultrasound. For the transducer elements 310, magnetostrictive ultrasonic transducers using magnetostrictive effects of a magnetic substance mainly used in ultrasound probe devices, piezoelectric ultrasonic transducers using piezoelectric effects of a piezoelectric material, piezoelectric micromachined ultrasonic transducers (pMUTs), or the like may be used, and capacitive micromachined ultrasonic transducers (cMUTs) transmitting and receiving ultrasound by means of vibration of hundreds or thousands of micromachined thin films may also be used. The cMUTs will be taken as an example of the transducer elements 310 in the present disclosure.

The transducer array 300 includes multiple transducer groups 305 with many cMUTs 310 arrayed in the form of a matrix, as shown in FIGS. 3 to 5.

The transducer groups 305 constitute the transducer array 300 by also being arrayed in the form of a matrix like the cMUTs 310.

A transducer group 305 formed by multiple cMUTs 310 arrayed in the matrix form is now referred to as a cMUT tile. In FIGS. 3 to 5, cMUTs 310 are arrayed in the form of a 4×4 matrix, i.e., in two dimension in a cMUT tile 305, but are not limited thereto and may be arrayed in one dimension (1D). Likewise, the cMUT tiles 305 may also be arrayed in 1D.

A gap (a) between cMUTs 310 arranged in a single cMUT tile 305 may be 250 μm or less, and a gap (b) between cMUTs 310 arranged in neighboring columns or rows of neighboring cMUT tiles 305 may be 500 μm or less.

The transducer array 300 is bonded in the integrated circuit 200, such as an application specific integrated circuit (ASIC) by a flip chip bonding method. The transducer array 300 in accordance with an embodiment of the disclosure is bonded on a single large-area ASIC 200 by the flip chip bonding method.

As shown in FIG. 5, the cMUT 310s are flip-chip bonded on the ASIC 200 with solder bumps 330. In the ASIC 200, there are driving elements 230 arranged as many as the number of the cMUTs 310 for driving the respective cMUTs 310, and the cMUTs 310 and the driving elements 230 are connected by flip chip bonding.

As shown in FIGS. 3 to 5, the ASIC 200 bonded with the transducer array 300 is installed on the printed circuit board 100. The ASIC 200 and the printed circuit board 100 may be combined by a wire bonding method. As shown in FIG. 5, the ASIC 200 and the printed circuit board 100 are connected by connecting pads 270, 170 arranged on both the ASIC 200 and the printed circuit board 100 via wires 171. As many pads 270, 170 as the number of rows or columns of the cMUTs 310 forming the transducer array 300 may be arranged on the ASIC 200 and the printed circuit board 100. If an electric signal is applied through the printed circuit board 100, the electric signal to be applied to the transducer array 300 may be adjusted according to the logic of the ASIC 200 to control transmission and reception of ultrasound.

As described above, the ASIC 200 may include as many driving elements 230 as the number of corresponding cMUTs 310 to drive the respective cMUTs 310. FIG. 6 shows an architecture of the ASIC 200 for transmission and reception of ultrasound, and FIG. 7 shows a detailed configuration of the driving element 230 shown in FIG. 6.

Referring to FIGS. 6 and 7, the ASIC 200 includes as many driving elements 230 as the number of corresponding cMUTs 310, and each driving element 230 includes detailed configuration for transmission and reception of ultrasound.

The driving element 230 may include an analog beamformer 234, a transmitter 232, a transmission/reception switch 231, and a receiver 233.

Beamforming refers to enhancing the strength of a signal by a method of superposition of ultrasounds in transmitting and receiving the ultrasounds with the plurality of transducer elements 310. If time for ultrasounds transmitted from the respective transducer elements 310 to be reflected off and return from a target portion differs, the ultrasounds for superposition are out of phase. Accordingly, signal amplification is not achieved by the superposition.

The analog beamformer 234 delays transmit/receive signals using a circuit element to make them in-phase. For example, ultrasounds transmitted by the respective transducer elements 310 of the transducer array 300 are superposed at a target portion by transmit beamforming, and the superposed ultrasound is reflected from the target portion and arrives back at the transducer elements 310.

Each transducer element 310 generates an ultrasound signal by converting the echo ultrasound back to an electric signal. Since the strength of the ultrasound signals generated in this way is very weak, the ultrasound signals need to be combined into one and analyzed as a single signal.

However, time for echo ultrasound to arrive at the respective transducer elements 310 differs because of a difference in distance to the target portion between the respective transducer elements 310, and consequently, time for the respective transducer elements 310 to generate an electric signal also differs.

Accordingly, to combine the electric signals output from the respective transducer elements 310 into a single signal, the electric signals from all the transducer elements 310 of the transducer array 300 are added together at a time when output of the electric signals is completed from all the transducer elements 310 of the transducer array 300 after the electric signals output from the respective transducer elements 310 are delayed in time as long as inversely proportional to the difference in distance between the respective transducer elements 310 and the target portion.

FIG. 8 is an exemplary configuration of the analog beamformer 234 of the ultrasound probe. A beamforming procedure will be described in more detail with reference to FIG. 8.

Referring to FIG. 8, time for the respective transducer elements 310 constituting the transducer array 300 to receive echo ultrasounds reflected off and returning from even the same target portion differs. That is, there exist certain time differences in reception of echo ultrasounds reflected from the same target portion.

The reason is that distances between the target portion and the respective transducer elements 310 TE1 to TE6 are not all the same. Thus, even if the respective transducer elements TE1 to TE6 receive echo ultrasounds at different points of time, the echo ultrasounds may have been reflected and returned from the same target portion. Accordingly, the time differences among the ultrasound signals generated by the respective transducer elements 310 TE1 to TE6 are to be corrected first.

The analog beamformer 234 may include a time difference corrector 235 for correcting the time difference between ultrasound signals by delaying the ultrasound signals, and a focusing unit 236 for focusing the ultrasound signals with the time difference corrected. For example, as shown in FIG. 8, the time difference corrector 235 delays transmission of an ultrasound signal input on a particular channel by a certain time such that ultrasound signals x input on respective channels reach the focusing unit 236 at the same time.

The focusing unit 236 focuses the ultrasound signals x whose time difference have been corrected.

Specifically, the focusing unit 236 focuses ultrasound signals by applying a predetermined weight, i.e., a beamforming coefficient for each input ultrasound signal to stress a signal at a particular position or attenuate signals in other positions. Accordingly, an ultrasound image may be created conforming to a user demand or user convenience.

In this case, the focusing unit 236 may focus the ultrasound signals using beamforming coefficients set independently of the ultrasound signals output by the transducer array 300 (data independent type beamforming).

Alternatively, ultrasound signals may be focused using optimal beam forming coefficients calculated based on the input ultrasound signals (adaptive beamforming).

A beamforming process performed in an ultrasound imaging device may be generally expressed as in the following equation 1:

$$z[n] = \sum_{m=0}^{M-1} w_m[n] x_m[n - \Delta_m[n]] \quad (1)$$

where n denotes a value of a position of the target portion, m denotes an identification number for a channel of an ultrasound signal collected by the transducer element 310, and $w_m[n]$ denotes a beamforming coefficient w applied to an ultrasound signal of an $m^{th}$ channel reflected from position n and collected by the $m^{th}$ transducer element 310. $\Delta m$ is a value of time delay, which delays transmission of an ultrasound signal input on a particular channel to a certain extent. Time delaying is performed in the time difference corrector 235 as described above. Accordingly, $x_m[n-\Delta_m[n]]$ refers to an ultrasound signal of each channel with the time difference corrected.

If time difference of an input signal is assumed to have already been corrected, the equation 1 may be rewritten into the following equation 2:

$$z = w^H x \quad (2)$$

Specifically, a general ultrasound beamforming corrects time differences of ultrasound signals x of the respective channels as written in the equations 1 and 2, applies certain weights to the signals with the time difference corrected, $x-\Delta x$, and outputs a focused ultrasound signal z.

The analog beamformer 234 uses time delay information stored in advance, if any, in correcting time difference with time delaying as described above, to delay ultrasounds for transmission from the plurality of transducer elements 310 and ultrasound signals generated by receiving echo ultrasounds from the plurality of transducer elements 310.

An element memory 239 stores the time delay information for beamforming. The analog beamformer 234 performs beamforming by delaying ultrasounds for transmission from the transducer elements 310 and ultrasound signals generated by receiving echo ultrasounds from the transducer elements 310, using the time delay information stored in the element memory 239.

Each element memory 239 may store different time delay information for beamforming for a transmit or receive signal of the corresponding transducer element 310, and the time delay information stored in each element memory 239 is output from a time delay table 250 installed on the ASIC 200.

The time delay table 250 is installed in the ASIC 200 using other area than the area where the transducer array 300 is installed, as shown in FIG. 4.

The time delay table 250 stores or calculates all the time delay information relating to beamforming to be performed by the analog beamformer 234 included in each driving element 230. The time delay table 250 is connected to the element memories of the respective driving elements 230 for outputting time delay information of the corresponding driving elements 230, and the analog beamformer 234 of each driving element 230 performs beamforming using the time delay information stored in the element memory 239.

The time delay table 250 may be implemented by a memory storing the time delay information of the respective driving elements 230, or by a lookup table including the memory. Furthermore, a calculation unit may be included for calculating the time delay information for the respective driving elements 230 and outputting the time delay information to the respective driving elements 230 each time ultrasound is transmitted or received. If it is hard to store the time delay information in advance in a memory because an amount of data of the time delay information for all the driving elements 230 is very huge, the calculation unit may calculate the time delay information for the respective driving elements 230 and outputting the time delay information to the respective driving elements 230 each time ultrasound is transmitted or received. Whenever the time delay information is changed, the time delay table 250 also outputs the changed time delay information to the element memory 239.

Arranging the time delay table 250 as well on the ASIC on which the transducer array 300 is installed may prevent delay of signals that may otherwise occur if the time delay table 250 is not arranged on the ASIC 200 but arranged off chip.

The transmitter 232 generates a signal for transmission using a transmit beam formed by the analog beamformer 234. The transmitter 232 may include a transmit pulser for generating a transmit pulse to be transmitted to the object ob from the ultrasound probe P.

In another example, if the transmitter 232 uses a low-voltage transmit pulse input from the main body M instead of the transmit pulser, it may include a high-voltage amplifier for amplifying the low-voltage pulse.

In other words, the transmitter 232 may directly include the transmit pulser, or may include the high-voltage amplifier to amplify a low-voltage pulse output from the outside instead of the transmit pulser.

The receiver 233 performs a predetermined processing job on echo ultrasound received from the transducer element 310. For example, the receiver 233 may include a low noise amplifier (LNA) for reducing noise of the analog signal received from the transducer element 310, or a variable gain amplifier (VGA) for controlling a gain value based on the input signal. In this regard, the VGA may be a time gain compensation (TGC) that compensates for a gain based on a distance to the target portion, without being limited thereto.

The transmission/reception switch 231 enables the transducer element 310 to transmit ultrasound according to the transmit pulse generated by the transmitter 232 or receive ultrasound reflected from the object ob by switching between signal transmission and reception of the transducer element 310, to allow an electric signal to go through a process, such as amplification, once the electric signal is generated by the transducer element 310.

As shown in FIG. 2, the main body M may include an image processor 400 for generating an image based on the beamformed ultrasound signal. The image processor 400 makes the object ob imaged for the user, e.g., a doctor or patient, to visually check the inside of the object ob, e.g., a human body, based on the beamformed ultrasound image z.

Specifically, the image processor 400 uses an ultrasound signal received by the transducer module T and beamformed by the beamformer 100 to generate and output an ultrasound image to a system memory 410 or the display d.

In addition, the image processor 400 may further perform extra image processing on the ultrasound image in some embodiments. For example, the image processor 400 may further perform post processing on the image, such as correcting or readjusting contrast, brightness, or sharpness of the ultrasound image.

It may also place an increasing emphasis on a particular portion of the ultrasound image, and may generate a three-dimensional ultrasound image using a plurality of ultrasound images after generating the plurality of ultrasound images. Such extra image processing of the image processor 400 may be performed according to predetermined settings, or in response to a user instruction or command input through the input unit i.

The system memory 410 may store the ultrasound image generated or separately post-processed by the image processor 400, and allow the ultrasound image to be displayed in the display d at the request of e.g., the user.

The display d may display the ultrasound image generated by the image processor 400 or stored in the system memory 410, thereby allowing the user to visually examine the internal structure or tissue of the object ob.

The main body M of the ultrasound imaging device may also include an ultrasound generation controller 430. The ultrasound generation controller 430 may generate and deliver a transmit pulse to the transducer module T in response to a command of e.g., the system controller 440. The transducer module T may generate and irradiate ultrasound to the object ob according to the transmit pulse output from the ultrasound generation controller. In this case, as described above, the transmitter 232 included in the driving element of the transducer module T may be equipped with the high-voltage amplifier to amplify the transmit pulse. Furthermore, as described above, the transmit pulse may be generated by the transmit pulser equipped in the transmitter 232 and delivered directly to the transducer array 300.

The ultrasound generation controller 430 may also generate a separate control signal for a power source 450 to apply an AC current to the transducer module T.

The system controller 440 is configured to control general operation of the ultrasound imaging device including the transducer module T, the ultrasound generation controller 430, the image processor 400, the system memory 410, the display d, etc.

In some embodiments, the system controller 440 may control operation of the ultrasound imaging device based on predetermined settings, and may control the ultrasound imaging device after generating a predetermined control command in response to the user's instruction or command input through a separate input unit i.

The input unit i receives predetermined instructions or commands from the user for controlling the ultrasound imaging device. The input unit i may include a user interface, such as e.g., a keyboard, a mouse, a trackball, a touch screen, a paddle, etc.

The invention claimed is:
1. An ultrasound probe comprising:
a transducer array including a plurality of transducer elements configured to transmit or receive ultrasound; and
an integrated circuit, in which the transducer array is bonded, including a plurality of driving elements corresponding to the plurality of transducer elements,
wherein the integrated circuit comprises a time delay table configured to output time delay information regarding respective ultrasound transmission and reception for each of the plurality of transducer elements, and
wherein the time delay table is installed in an area other than an area where the transducer array is installed on the integrated circuit.
2. The ultrasound probe of claim 1,
wherein each of the plurality of driving elements comprises,
an element memory configured to store the time delay information output from the time delay table; and
a beamformer configured to perform beamforming based on the time delay information stored in the element memory.
3. The ultrasound probe of claim 1,
wherein each of the plurality of driving elements comprises,
one of a transmit pulser configured to generate a pulse for ultrasound transmission of the transducer element and an amplifier configured to amplify an externally input pulse.
4. The ultrasound probe of claim 1,
wherein each of the plurality of driving elements comprises a pre-amplifier configured to amplify an echo ultrasound signal received by the transducer element.
5. The ultrasound probe of claim 1,
wherein the time delay table comprises a memory configured to store time delay information regarding respective ultrasound transmission and reception of the plurality of transducer elements.
6. The ultrasound probe of claim 1,
wherein the time delay table comprises a calculation unit configured to calculate time delay information regarding respective ultrasound transmission and reception of the plurality of transducer elements.
7. The ultrasound probe of claim 1,
further comprising: a printed circuit board where the integrated circuit is installed.
8. The ultrasound probe of claim 1,
wherein the transducer array comprises a plurality of transducer groups including the plurality of transducer elements.
9. The ultrasound probe of claim 8,
wherein the transducer groups are arranged in one of an one-dimensional (1D) array and a two-dimensional (2D) array, and
the transducer elements included in the transducer group are arranged in one of a one-dimensional (1D) array and a two-dimensional (2D) array.
10. The ultrasound probe of claim 1,
wherein the transducer element comprises one of piezo-electronic transducer (PZT), capacitive micromachined ultrasonic transducer cMUT), monocrystal, and piezo-electric micromachined ultrasonic transducer (pMUT).
11. An ultrasound imaging device comprising:
an ultrasound probe comprising:

a transducer array including a plurality of transducer elements configured to transmit or receive ultrasound, an integrated circuit, in which the transducer array is bonded, including a plurality of driving elements corresponding to the plurality of transducer elements, and a time delay table configured to output time delay information regarding respective ultrasound transmission and reception for each of the plurality of transducer elements; and a main body configured to generate an ultrasound image based on a signal output from the ultrasound probe, wherein the time delay table is installed in an area other than an area where the transducer array is installed on the integrated circuit.

12. The ultrasound imaging device of claim 11, wherein each of the plurality of driving elements comprises, an element memory configured to store the time delay information output from the time delay table, and a beamformer configured to perform beamforming based on the time delay information stored in the element memory.

13. The ultrasound imaging device of claim 12, wherein the beamformer is configured to output a beamformed signal to the main body, and wherein the main body comprises an image processor configured to receive the beamformed signal to generate an ultrasound image.

14. The ultrasound imaging device of claim 11, wherein each of the plurality of driving elements comprises, a transmit pulser configured to generate a pulse for ultrasound transmission of the transducer element.

15. The ultrasound imaging device of claim 11, wherein the main body comprises an ultrasound generation controller configured to output a pulse for ultrasound transmission of the transducer element, and wherein the ultrasound probe comprises an amplifier configured to amplify the pulse output from the ultrasound generation controller.

16. The ultrasound imaging device of claim 11, wherein the time delay table comprises a memory configured to store time delay information regarding respective ultrasound transmission and reception of the plurality of transducer elements.

* * * * *